United States Patent
Holmes et al.

(10) Patent No.: US 9,689,844 B2
(45) Date of Patent: Jun. 27, 2017

(54) ULTRASONIC INSPECTION USING FLEXIBLE TWO-DIMENSIONAL ARRAY APPLIED ON SURFACE OF ARTICLE

(71) Applicant: The Boeing Company, Chicago, IL (US)

(72) Inventors: Tyler M. Holmes, Seattle, WA (US); Jeffrey R. Kollgaard, Seattle, WA (US); Gary E. Georgeson, Tacoma, WA (US)

(73) Assignee: The Boeing Company, Chicago, IL (US)

(*) Notice: Subject to any disclaimer, the term of this patent is extended or adjusted under 35 U.S.C. 154(b) by 101 days.

(21) Appl. No.: 14/809,522

(22) Filed: Jul. 27, 2015

(65) Prior Publication Data

US 2017/0030863 A1    Feb. 2, 2017

(51) Int. Cl.
| | |
|---|---|
| *G01N 29/04* | (2006.01) |
| *G01N 29/265* | (2006.01) |
| *G01N 29/30* | (2006.01) |
| *G01N 29/22* | (2006.01) |
| *G01N 29/24* | (2006.01) |
| *G01N 29/44* | (2006.01) |

(52) U.S. Cl.
CPC ......... *G01N 29/041* (2013.01); *G01N 29/043* (2013.01); *G01N 29/226* (2013.01); *G01N 29/2468* (2013.01); *G01N 29/2481* (2013.01); *G01N 29/265* (2013.01); *G01N 29/30* (2013.01); *G01N 29/4427* (2013.01); *G01N 2291/106* (2013.01); *G01N 2291/2638* (2013.01)

(58) Field of Classification Search
None
See application file for complete search history.

(56) References Cited

U.S. PATENT DOCUMENTS 6,115,624 A * 9/2000 Lewis .................... A61B 5/035
                                                    600/376
7,478,569 B2   1/2009 Bossi et al.
(Continued)

FOREIGN PATENT DOCUMENTS

EP    2645094 A2    10/2013

OTHER PUBLICATIONS

Extended European Search Report dated Jan. 30, 2017 in European Patent Application No. 16180142.8 (European counterpart to the instant patent application).

*Primary Examiner* — Robert R Raevis
(74) *Attorney, Agent, or Firm* — Ostrager Chong Flaherty & Broitman P.C.

(57) ABSTRACT

Methods for ultrasonic inspection of a structure by laying a flexible two-dimensional flexible ultrasonic transducer array over a damage site on the structure with minimal physical interaction with the array during set-up and without further movement of the array during data acquisition. In addition, the array may remain in place on a difficult-to-access surface to enable easy periodic inspections over a long period of time. In some embodiments, the array is sandwiched between a flexible delay line substrate and a flexible display panel. In accordance with one wireless embodiment, a GPS receiver, a transceiver, pulser/receiver circuitry, and a source of electrical power (e.g., a battery) are attached to a portion of the flexible delay line substrate that extends beyond one edge of the array.

11 Claims, 10 Drawing Sheets

(56) References Cited

U.S. PATENT DOCUMENTS

| | | |
|---|---|---|
| 7,593,086 B2 | 9/2009 | Jeong et al. |
| 7,617,730 B2 | 11/2009 | Georgeson |
| 7,712,369 B2 | 5/2010 | Georgeson |
| 8,453,928 B2 | 6/2013 | Melandso et al. |
| 8,662,395 B2 | 3/2014 | Melandso et al. |
| 2007/0125189 A1 | 6/2007 | Bossi et al. |
| 2008/0309200 A1 | 12/2008 | Melandso et al. |
| 2010/0256456 A1 | 10/2010 | Natarajan |
| 2014/0249414 A1* | 9/2014 | Herzog ................ A61B 5/0095 600/440 |
| 2015/0374328 A1* | 12/2015 | Ginestet ............... A61B 5/0011 600/301 |

* cited by examiner

ULTRASONIC INSPECTION USING FLEXIBLE TWO-DIMENSIONAL ARRAY APPLIED ON SURFACE OF ARTICLE

BACKGROUND

This invention generally relates to systems and methods for ultrasonic inspection of manufactured articles, and in particular, to methods for ultrasonic inspection of damaged structure underlying non-planar surfaces.

Non-destructive inspection (NDI) of structures involves examining a structure without harming the structure or requiring significant disassembly. Non-destructive inspection is typically preferred to avoid the time and costs associated with the removal of a part for inspection and to avoid the potential for causing damages when inspection is needed. Non-destructive inspection is used in the aircraft industry to inspect aircraft structures such as composite structures and bonded panels. Inspections may identify defects such as cracks, discontinuities, disbonds between layers, voids, and areas having undesirable porosity. Preventive inspections may be performed during manufacturing and at any time during the service life of an aircraft structure to validate the integrity and fitness of the structure. Inspections may also be prompted by incidents such as collisions and ballistic impacts that are suspected or known to cause damages.

Various types of ultrasonic methods are used to perform non-destructive inspections. For example, a structure may be inspected by a pulse-echo method wherein a sensor device sends ultrasonic pulses into a structure and receives echo pulses that reveal the condition of the structure. Data acquired by such a sensor device can be processed and presented to an operator. B-scan images can be produced that reveal depth characteristics of an inspected structure. C-scan images can be produced to reveal a mapping of the inspected structure. These images can reveal features that are not easily perceived or characterized by simple visual inspection of the exterior of a structure. Collecting data for B-scan and C-scan images typically entails moving a sensor along a portion of a structure in order to collect data across an area of the inspected structure.

Two-dimensional arrays of ultrasonic pulse-echo sensors have been developed and employed in NDI procedures. Such arrays provide numerous sensors regularly distributed across an area and each sensor can collect location-specific data. Thus, a mapping of a portion of the interior structure of a manufactured article can be obtained without movement of the sensors.

When inspecting a structure, a display is typically needed in order to view images of the structure being inspected. For example, on-site inspection may require a computer or laptop having a screen for viewing displayed images and processing data associated with the displayed images. However, the image display information must be accurately transferred to registered locations in the structure.

It would therefore be advantageous to provide an ultrasonic inspection system that is capable of accurately transferring a displayed image onto a structure. In addition, it would be advantageous to provide an ultrasonic inspection system that is portable, lightweight and capable of inspecting structures effectively and efficiently with the results displayed proximate to the inspection zone. Furthermore, it would be advantageous to provide an ultrasonic inspection system that is economical to manufacture and use. In addition, it would be advantageous to provide simple methods for ultrasonic inspection of a structure by disposition of a flexible sensor array overlying a damage site on the structure with minimal physical interaction with the array during set-up and without further movement of the array during data acquisition. In addition, it would be advantageous to provide simple one-sided ultrasonic inspection methods for detecting and characterizing damage beneath contoured surfaces of structures in cases where access to the damage site is limited.

SUMMARY

The subject matter disclosed in detail below is directed to systems, methods and devices for ultrasonic inspection of a structure which achieve the advantageous features mentioned above. In particular, a flexible ultrasonic transducer device can be laid against and acoustically coupled to a damage site on the structure with minimal physical interaction with the device during set-up by a technician and without further movement of the device during data acquisition. In addition, the flexible ultrasonic inspection device may remain in place on a difficult-to-access surface to enable easy periodic inspections over a long period of time.

In accordance with one some embodiments, the ultrasonic transducer device comprises a flexible two-dimensional flexible ultrasonic transducer array having a flexible delay line substrate attached to one side of the flexible ultrasonic transducer array. In other embodiments, the flexible ultrasonic transducer array is sandwiched between the flexible delay line substrate and a flexible display panel. In accordance with one wireless embodiment, a GPS receiver, a transceiver, pulser/receiver circuitry, and a source of electrical power (e.g., a battery) are attached to a portion of the flexible delay line substrate that extends beyond one edge of the flexible ultrasonic transducer array.

In addition, the inspection methods disclosed herein may include an automated process for calibrating the ultrasonic inspection device using three-dimensional (3-D) model data of the structure to be inspected. This will make it possible for technicians without NDI training to set-up the inspection device at the inspection site. Automated calibration reduces lead time, since there will be no need to wait for an off-site trained NDI inspector to arrive at the inspection site, and time is also saved through the automation of the calibration process. Automated calibration also reduces the potential for human error.

One aspect of the subject matter disclosed in detail below is an ultrasonic inspection device comprising: a flexible assembly comprising a flexible ultrasonic transducer array having first and second faces, and a flexible delay line substrate acoustically coupled to the first face of the flexible ultrasonic transducer array; data acquisition module configured to control pulsing of and data acquisition by the flexible ultrasonic transducer array; a global positioning system receiver configured to determine a location of the global positioning system receiver; a transceiver configured to communicate with the data acquisition module and the global positioning system receiver; and a battery electrically coupled to the data acquisition module, the global positioning system receiver, and the transceiver for providing power thereto, wherein the data acquisition module, the global positioning system receiver, the transceiver, and the battery are physically attached to the flexible assembly. The ultrasonic inspection device may further comprise adhesive adhered to portions of a surface of the flexible delay line substrate that faces away from the flexible ultrasonic transducer array.

In accordance with some embodiments of the ultrasonic inspection device described in the preceding paragraph, the flexible assembly further comprises a flexible display panel overlapping at least a portion of the second face of the flexible ultrasonic transducer array, and the data acquisition module is further configured to receive ultrasonic data from the flexible ultrasonic transducer array in a first format, convert the ultrasonic data in the first format to ultrasonic data in a second format suitable for display, and send the ultrasonic data in the second format to the flexible display panel. The data acquisition module comprises: pulser/receiver circuitry electrically coupled to receive the ultrasonic data in the first format from the flexible ultrasonic transducer array; and a processor programmed to convert the ultrasonic data in the first format to ultrasonic data in the second format and control the flexible display panel to display the ultrasonic data in the second format. The flexible display panel comprises a polymeric substrate, a multiplicity of pixels arranged in rows and columns in or on the polymeric substrate, and a multiplicity of thin-film transistors disposed in or on the polymeric substrate and electrically coupled to respective pixels of the multiplicity of pixels. The pixels may comprise respective organic light-emitting diodes or liquid crystal.

In some embodiments of the ultrasonic inspection device, the data acquisition module, the global positioning system receiver, the transceiver, and the battery are physically attached to a portion of the flexible delay line substrate that extends beyond a perimeter of the flexible ultrasonic transducer array.

Another aspect of the subject matter disclosed in detail below is a system comprising: a structural component (e.g., part of an aircraft) having a contoured surface; a flexible assembly affixed to the contoured surface of the structural component, the flexible assembly comprising a flexible ultrasonic transducer array having first and second faces, and a flexible delay line substrate having first and second faces, the first face of the flexible delay line substrate being affixed to the contoured surface of the structural component and the second face being acoustically coupled to the first face of the flexible ultrasonic transducer array; an external module comprising a source of electrical power, a transceiver for transmitting and receiving data, and a data acquisition device configured to communicate with the transceiver; and an electrical cable connecting the flexible ultrasonic transducer array to the data acquisition device, the electrical cable having plugs at opposing ends thereof capable of being coupled to and uncoupled from the flexible assembly and the external module, wherein the data acquisition device is configured to communicate with the flexible ultrasonic transducer array via the electrical cable. This system may further comprise a display panel, wherein the data acquisition device is further configured to control the display panel to display ultrasonic data acquired by the flexible ultrasonic transducer array. The display panel may be part of the external module or part of the flexible assembly. In the former case, the display panel will be referred to herein as a "display monitor"; in the latter case, the display panel will be referred to herein as a "flexible display panel".

A further aspect is a system comprising: a structural component (e.g., part of an aircraft) having a contoured surface; a flexible assembly affixed to a portion of the contoured surface of the structural component, the flexible assembly comprising a flexible ultrasonic transducer array having first and second faces, and a flexible delay line substrate having first and second faces, the first face of the flexible delay line substrate being affixed to the contoured surface of the structural component and the second face being acoustically coupled to the first face of the flexible ultrasonic transducer array; a data acquisition module configured to control pulsing of and data acquisition by the flexible ultrasonic transducer array; a global positioning system receiver configured to determine a location of the global positioning system receiver and output location data represent that location; a transceiver configured to communicate with the data acquisition module and to receive the location data from the global positioning system receiver; and a computer system programmed to receive the location data from the transceiver, and then generate or retrieve a calibration file containing calibration data which is a function of material properties of a portion of the structural component beneath the portion of the contoured surface.

Yet another aspect is a method for calibrating an ultrasonic inspection device, comprising: (a) storing structural model data representing material properties of a structure as a function of location in a coordinate system of the structure; (b) attaching a flexible ultrasonic inspection device to a surface of a portion of the structure, wherein the flexible ultrasonic inspection device comprises a flexible substrate, a two-dimensional flexible ultrasonic transducer array attached to the flexible substrate, and a global positioning system receiver attached to the flexible substrate; (c) acquiring location data using the global positioning system receiver, the location data representing a location of the global positioning system; (d) sending the acquired location data to a computer system at a remote location; (e) determining a location of the flexible ultrasonic inspection device in the coordinate system of the structure; (f) retrieving structural model data representing material properties of the structure in proximity to the location of the flexible ultrasonic inspection device in the coordinate system of the structure; (g) generating or retrieving a calibration file containing calibration data which is a function of the retrieved structural model data representing material properties of the portion of the structure in proximity to the location of the flexible ultrasonic inspection device; (h) sending the calibration file to a data acquisition module that is configured to communicate with the flexible ultrasonic transducer array; and (i) calibrating the data acquisition module using calibration data from the calibration file.

A further aspect is a method for ultrasonic inspection of multiple sites in a structure, comprising: (a) attaching a first flexible ultrasonic inspection device to a surface of a first portion of the structure, wherein the first flexible ultrasonic inspection device comprises a first flexible substrate and a first two-dimensional flexible ultrasonic transducer array attached to the first flexible substrate; (b) attaching a second flexible ultrasonic inspection device to a surface of a second portion of the structure, wherein the second flexible ultrasonic inspection device comprises a second flexible substrate and a second two-dimensional flexible ultrasonic transducer array attached to the second flexible substrate; (c) connecting a module to the first flexible ultrasonic inspection device via an electrical cable, which module comprises pulser/receiver circuitry which is configured to control interrogation and data acquisition by the first flexible ultrasonic transducer array during inspection of the first portion of the structure and is further configured to control interrogation and data acquisition by the second flexible ultrasonic transducer array during inspection of the second portion of the structure; (d) controlling the first flexible ultrasonic transducer array to interrogate and acquire data from the first portion of the structure while the module is connected to the first flexible ultrasonic inspection device; (e) disconnecting the electrical cable from the first flexible ultrasonic inspection device after completion of step (d); (f) connecting the module to the second flexible ultrasonic inspection device via the electrical cable; and (g) controlling the second flexible ultrasonic transducer array to interrogate and acquire data from the second portion of the structure while the module is connected to the second flexible ultrasonic inspection device. This method may further comprise: (h) disconnecting the electrical cable from the second flexible ultrasonic inspection device after completion of step (g); and (i) repeating steps (c) through (h) at a later time, wherein the first and second flexible ultrasonic inspection device are not removed after steps (a) and (b) and before step (i).

Other aspects of methods for ultrasonic inspection using flexible two-dimensional flexible ultrasonic transducer arrays are disclosed and claimed below.

BRIEF DESCRIPTION OF THE DRAWINGS

The features, functions and advantages discussed in the preceding section can be achieved independently in various embodiments or may be combined in yet other embodiments. Various embodiments will be hereinafter described with reference to the drawings which illustrate at least some of the above-described and other aspects and in which similar elements in different drawings bear the same reference numerals.

DETAILED DESCRIPTION

Figure 1:
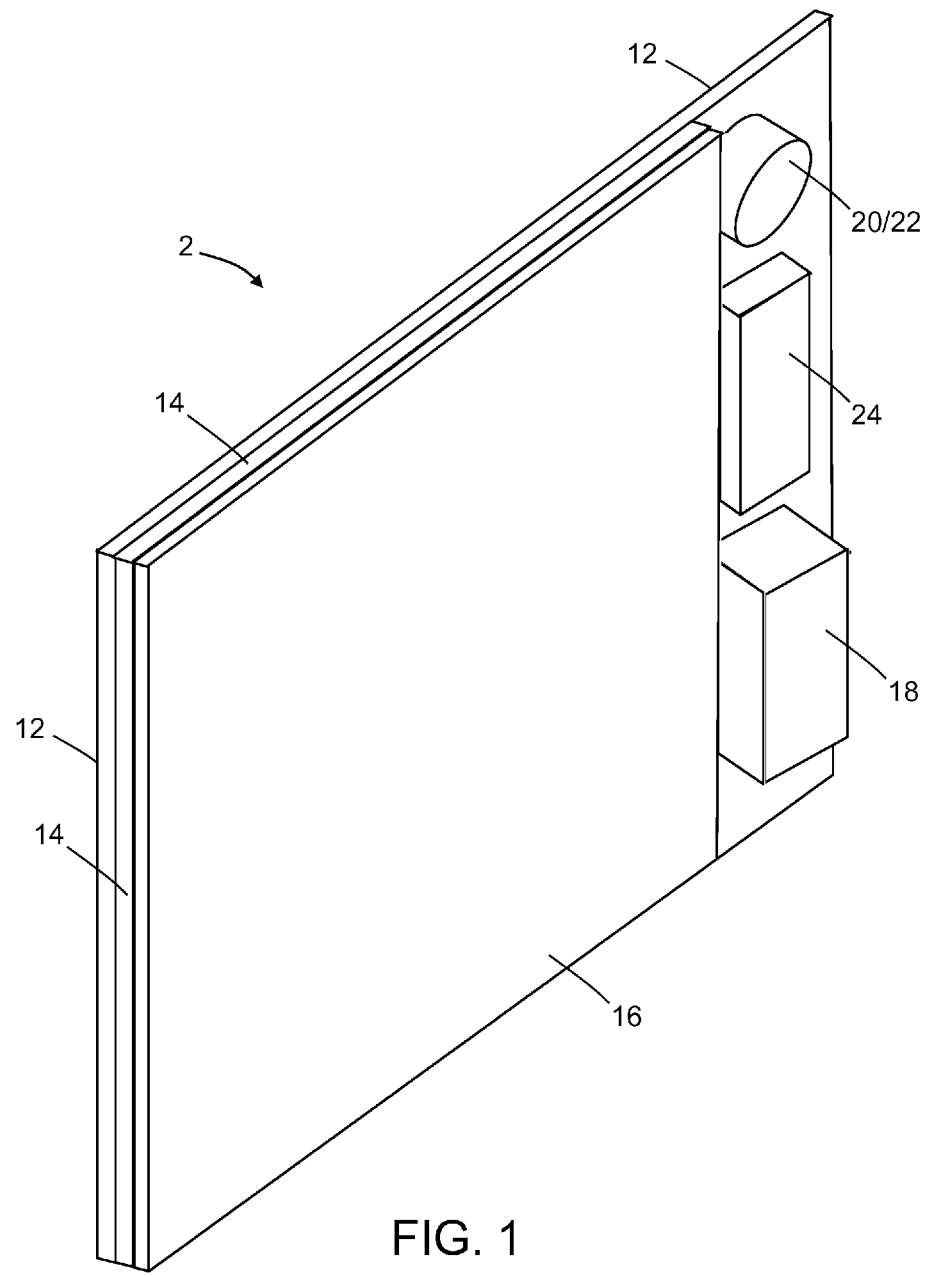
FIG. 1 is a diagram representing an isometric view of a wireless flexible ultrasonic inspection device in accordance with one embodiment.

In accordance with a first embodiment depicted in FIG. 1, a wireless flexible ultrasonic inspection device 2 is designed to conform to a surface in an area where a structure (e.g., a fuselage or wing of an aircraft, a hull of a boat, or a portion of some other type of structure) is to be inspected. This area may contain damage or defects in the structure underlying the surface area of the inspection site. In particular, the ultrasonic inspection device 2 may be especially useful when the inspection site is difficult to access.

The ultrasonic inspection device 2 depicted in FIG. 1 comprises a flexible ultrasonic transducer array 14 having first and second faces, a flexible delay line substrate 12 acoustically coupled to the first face of the flexible ultrasonic transducer array 14, and a flexible display panel 16 capable of overlapping at least a portion of the second face of the flexible ultrasonic transducer array 14. The periphery of the flexible delay line substrate 12 may define a gasket for contacting an inspected structure and tentatively adhering the ultrasonic inspection device 2 to the structure when intervening air is removed by an optional vacuum system accessory. Alternatively, peripheral margin portions of the flexible delay line substrate 12 can be taped or otherwise tentatively adhered (e.g., using adhesive) to an inspected structure by an adhesive material. As a further alternative, the ultrasonic inspection device 2 can be held in place by a clamp or bracket.

Figure 2A:
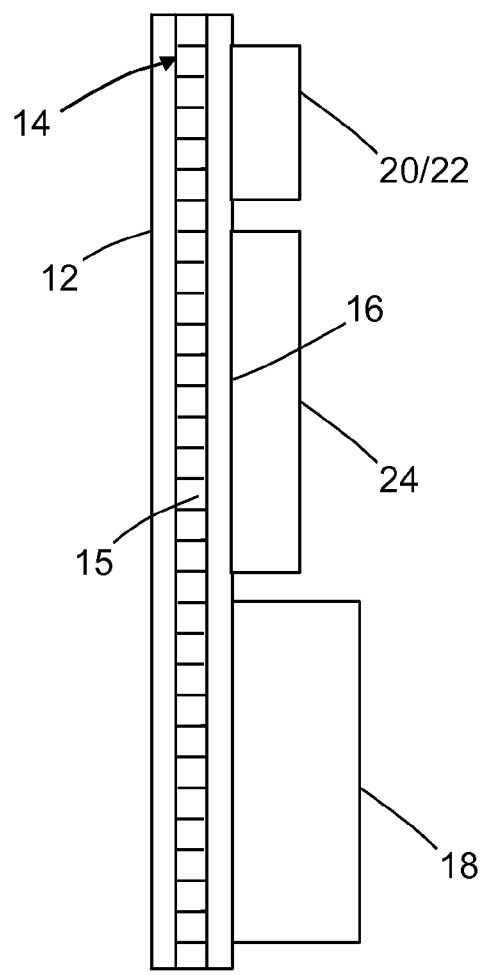
FIG. 2A is a diagram representing a sectional view of a wireless flexible ultrasonic inspection device having a multiplicity of ultrasonic transducer array arranged in rows and columns.

In accordance with some embodiments, the flexible ultrasonic transducer array 14 comprises a multiplicity of ultrasonic transducer elements 15 arranged in rows and columns, as depicted in the sectional view of FIG. 2A. The ultrasonic transducer elements 15 can be attached directly to the flexible delay line substrate 12 (as shown in FIG. 2A). Alternatively, the ultrasonic transducer elements 15 can be attached to, integrated with, printed on or embedded in a flexible substrate (not shown in FIG. 2A) which is attached to the flexible delay line substrate 12. For example, that flexible substrate could be a thin sheet of polymeric material, such as polyvinylidene fluoride ("PVDF"). Providing a flexible sheet of material allows the flexible ultrasonic transducer array 14 to be manipulated to conform to a variety of surface contours during an inspection procedure, as well as maintain intimate contact with the underlying structure.

In accordance with some embodiments, the flexible display panel 16 comprises a polymeric substrate, a multiplicity of pixels arranged in rows and columns in or on the polymeric substrate, and a multiplicity of thin-film transistors disposed in or on the polymeric substrate and electrically coupled to respective pixels of the multiplicity of pixels. For example, the pixels may comprise respective organic light-emitting diodes or liquid crystal.

The ultrasonic inspection device 2 depicted in FIG. 1 is self-contained and self-powered in the sense that a battery 18, a module comprising a GPS receiver 20 and a transceiver 22, and a data acquisition module 24 are all attached to an extension portion of the flexible delay line substrate 12. The data acquisition module 24 is configured to receive ultrasonic data from the flexible ultrasonic transducer array 14 in a first format, convert the ultrasonic data in the first format to ultrasonic data in a second format suitable for display, and then send the ultrasonic data in the second format to the flexible display panel 16. The transceiver 22 is configured to communicate with the data acquisition module 24 and the global positioning system receiver 20. The battery 18 is electrically coupled to the data acquisition module 24, the global positioning system receiver 20, and the transceiver 22 for providing power to the system components. As best seen in FIG. 1, the data acquisition module 24, the global positioning system receiver 20, the transceiver 22, and the battery 18 are physically attached to the flexible assembly. These physical attachments should be designed to minimize any decrease in the flexibility of the portion of the flexible delay line substrate 12 that extends beyond a perimeter of the flexible ultrasonic transducer array 14.

Referring to FIG. 2A, the flexible ultrasonic transducer array 14 may be configured for use in a pulse-echo mode. Thus, the ultrasonic transducer elements 15 would transmit and receive ultrasonic signals generally perpendicular to the surface of the structure being inspected. In the alternative, the flexible ultrasonic transducer array 14 may be configured for use in a pitch-catch mode. For instance, the ultrasonic transducer elements 15 could be arranged so one ultrasonic transducer element transmits an ultrasonic signal into the structure at an acute angle and the return ultrasonic signal is picked up by a receiving ultrasonic transducer element.

The ultrasonic transducer elements 15 may be arranged in a variety of configurations. As the distance between the ultrasonic transducer elements 15 decreases, the smaller the flaw that may be detected. Therefore, the spacing of the ultrasonic transducer elements 15 may be varied depending on the size of the flaw to be detected and to achieve a particular resolution of the inspection image.

Figure 2B:
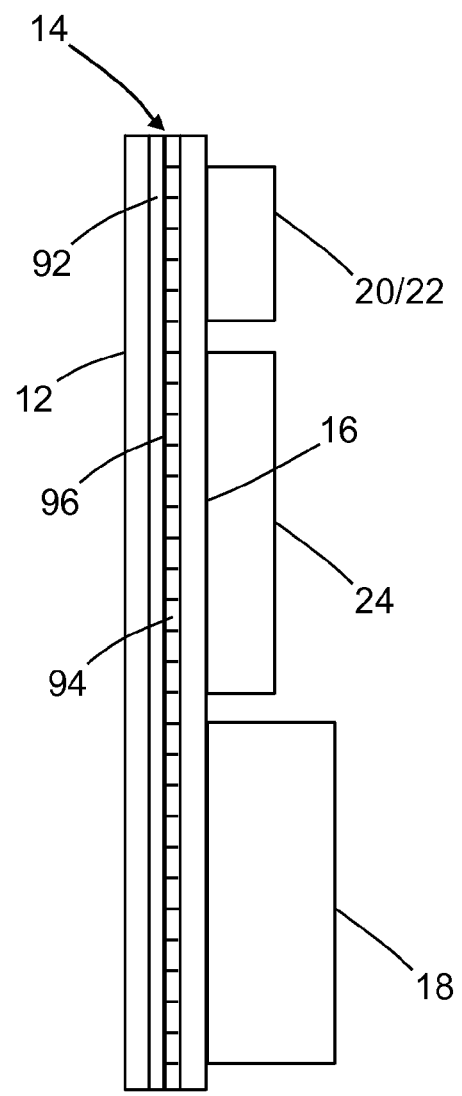
FIG. 2B is a diagram representing a sectional view of a wireless flexible ultrasonic inspection device having an ultrasonic transducer array comprising mutually orthogonal strip-shaped transmit and receive transducer elements.

In accordance with other embodiments, the flexible ultrasonic transducer array 14 comprises a plurality of mutually parallel strip-shaped transmit transducer elements 94 and a plurality of mutually parallel strip-shaped receive transducer elements (orthogonal to the transmit transducer elements) which are acoustically coupled by a flexible substrate 96 (e.g., a thin layer, a sheet, or a spray-on film) of an acoustic coupling medium, as depicted in the sectional view of FIG. 2B.

In the alternative, the flexible ultrasonic transducer array 14 depicted in FIG. 2B may be of the type disclosed in U.S. Patent Application Publ. No. 2008/0309200 (the disclosure of which is incorporated by reference herein in its entirety). That ultrasonic transducer array comprises one transmitter layer, one receiver layer, and two ground planes. The transmitter layer comprises a set of mutually parallel elongated electrodes disposed on the upper surface of a first layer of piezoelectric material (e.g., a film made of polyvinylidene fluoride) and a first planar electrode disposed on the lower surface of the first layer of piezoelectric material. Similarly, the receiver layer comprises a set of mutually parallel elongated receive electrodes disposed on the lower surface of a second layer of piezoelectric material and a second planar electrode disposed on the upper surface of the second layer of piezoelectric material. These transmitter and receiver layers are in turn adhered to upper and lower surfaces of a flexible substrate 96. The elongated transmit elements 94 of the transmitter layer overlie and cross over the elongated receive elements 92 of the receiver layer, thereby providing a matrix of overlapping intersections/pixels which constitute signal points of the flexible ultrasonic transducer array 14. The elongated electrodes of the transmit elements 94 overlap with the elongated receive elements 92 to form a matrix of individual transducer elements capable of transmitting and receiving ultrasonic waves at their respective locations in the matrix. The transmission and reception of ultrasonic waves must be done in separate operations using multiplexers (not shown) which connect the transmit electrodes to a signal source and connect the receive electrodes to a signal processor. The elongated transmit elements 94 transmit and the elongated receive elements 92 receive alternatingly, the elements in each set incrementing across the matrix. This arrangement uses less processing power and less cabling than an ultrasonic transducer array comprising multiple rows of transducer elements, each row comprising a respective multiplicity of transducer elements.

The flexible ultrasonic transducer array 14 is capable of detecting a flaw in a structure and communicating acquired ultrasonic data indicative of the flaw to the data acquisition device 24. In accordance with one embodiment, the data acquisition module 24 comprises: pulser/receiver circuitry electrically coupled to receive the ultrasonic data in the first format from the flexible ultrasonic transducer array 14; and a processor programmed to convert the ultrasonic data in the first format to ultrasonic data in the second format and control the flexible display panel 16 to display the ultrasonic data in the second format. The flexible display panel 16 may be positioned adjacent to the flexible ultrasonic transducer array 14 and is capable of generating various images of a portion of the underlying structure based on information generated by the data acquisition device 24.

The ultrasonic inspection device 2 can be used to inspect any number of structures in a variety of industries where detection of flaws or defects in the structure is required, such as in the aircraft, automotive, marine, or construction industries. The ultrasonic transducer array is capable of detecting any number of flaws or defects within or on the surface of the structure, such as impact damage (e.g., delaminations and matrix cracking), disbonds (e.g., airframe/reinforcing members or honeycomb composites), discontinuities, voids, or porosity, which could adversely affect the performance of the structure.

The term "structure" is not meant to be limiting, as the ultrasonic inspection device 2 could be used to inspect any number of parts or structures of different shapes and sizes, such as machined forgings, castings, pipes, or composite panels or parts. The inspection could be performed on newly manufactured structures or existing structures that are being inspected as part of a maintenance program. In addition, the structure could include various components. For instance, the structure could include a substructure for providing additional support to a structure. Further, the structure could be any number of materials. For example, the structure could be a metallic material, such as aluminum, or a composite material, such as graphite-epoxy. Moreover, the structure could be a portion of an aircraft made of composite material (e.g., a fuselage or a wing).

The data acquisition module 24 comprises a processor or similar computing device operating under the control of software so that data acquired by the flexible ultrasonic transducer array 14 may be converted to C-scan image data. Furthermore, the data acquisition module 24 comprises pulser/receiver circuitry, or similar device, so that the ultrasonic transducer elements are capable of transmitting ultrasound waves into and receiving returned ultrasound waves from the inspected structure. The flexible ultrasonic transducer array 14 communicates with the data acquisition module 24 via electrical conductors (not shown in the drawings). The data acquisition module 24 in turn communicates with the flexible display panel 16 and the transceiver 22 via electrical conductors (not shown in the drawings).

The flexible display panel 16 is positioned adjacent to the flexible ultrasonic transducer array 14. Because the flexible display panel 16, like the flexible ultrasonic transducer array 14, is flexible or pliable, the flexible display panel is also capable of conforming to a variety of surface contours of the structure under inspection. The flexible display panel 16 may extend to the outer perimeter of the flexible ultrasonic transducer array 14 so that the flexible display panel 16 is capable of displaying images resulting from data acquired by each of the ultrasonic transducer elements and, in particular, in a one-to-one actual-size format. However, the flexible display panel 16 could be various sizes and configurations for different inspection applications and structures.

The flexible display panel 16 is capable of displaying an image indicative of the structure being inspected by the flexible ultrasonic transducer array 14. Thus, technicians are capable of readily identifying the location and characteristics of any flaw, defect, or the like without having to refer to a remotely located display, such as a computer screen, and then attempt to transfer the location of the damaged area from the remotely located display to the structure. As a result, technicians may repair/replace the damaged area(s) on the structure or mark the damaged area(s) with a marking device, such as a pen or paint. For instance, the vacuum applied to the flexible delay line substrate 12 may be released so that the ultrasonic inspection device 2 may be partially or completely peeled away from the structure, and the technician may mark the location of the damaged area(s) accordingly. Consequently, the technician may immediately repair or replace the damaged area(s).

The data acquisition module 24 generates information indicative of the underlying structure, including, for example, flaws detected within the structure, based on data acquired by the flexible ultrasonic transducer array 14 and provides the flexible display panel 16 with the information to display an image, such as an ultrasonic C-scan.

Figure 3:
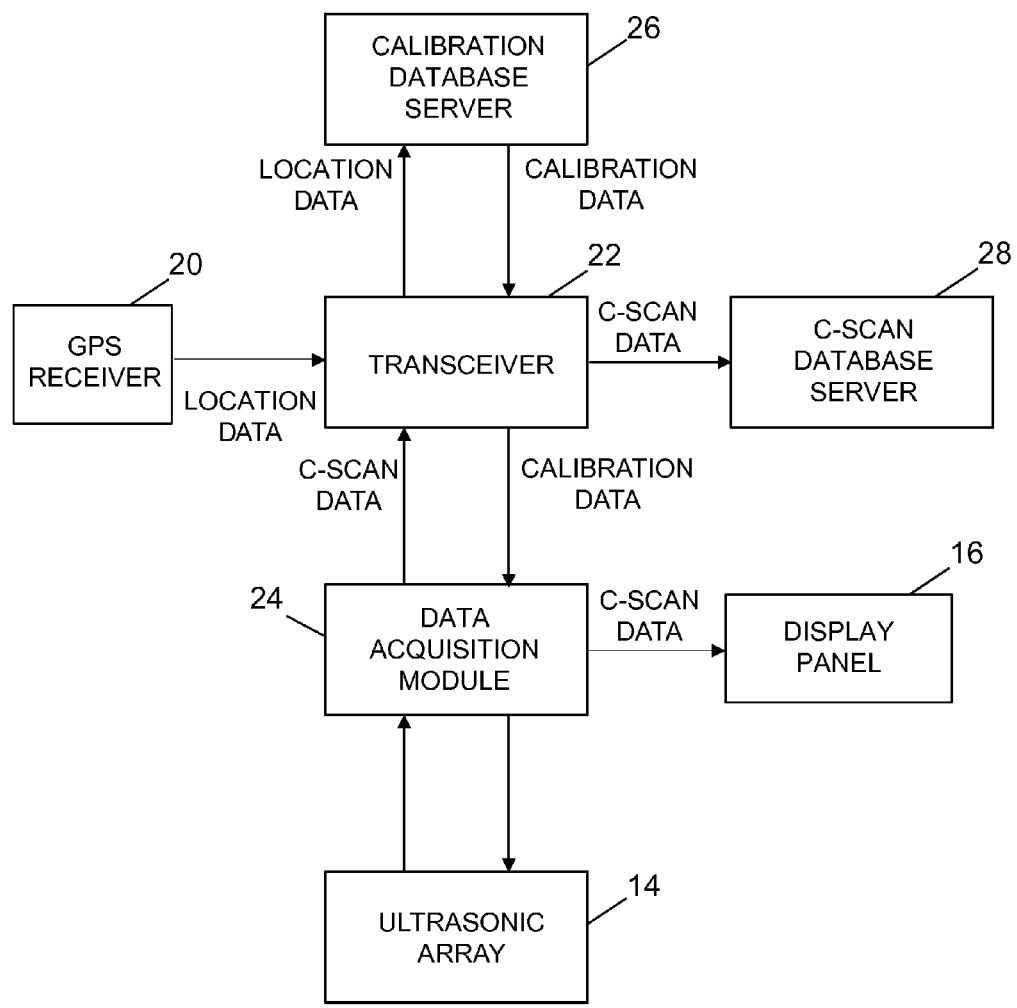
FIG. 3 is a block diagram identifying some components of a system that includes external servers and a wireless flexible ultrasonic inspection device that can communicate wirelessly with the external servers for obtaining calibration data and storing C-scan data.

FIG. 3 is a block diagram identifying components of a system that includes a wireless flexible ultrasonic inspection system of the type shown in FIG. 1 that communicates via a transceiver 22 with a calibration database server 26 for obtaining calibration data and with a C-scan database server 28 for storing C-scan data.

More specifically, the GPS receiver 20 determines its location and sends location data representing that location to the transceiver 22. A GPS receiver is an autonomous instrument that receives ranging signals broadcast from a constellation of GPS satellites and transforms those ranging signals into a location of the GPS receiver. The receiver's processor contains executable code to generate a pseudo-range or a line-of-sight distance to each satellite. To compute the location of the GPS receiver (which location establishes the location of the flexible ultrasonic transducer array 14), the GPS receiver determines the pseudo-range to three or more GPS satellites. The location data that GPS receiver 20 sends to transceiver 22 can be used to generate or retrieve a calibration file adapted for correctly calibrating the ultrasonic inspection device with respect to the actual structure being inspected.

The transceiver 22 transmits the location data to a calibration database server 26. The calibration database server 26 may also receive location data from other GPS receivers attached to different portions of the structure (e.g., an aircraft) being inspected. In accordance with one embodiment, the calibration database server 26 may comprise a processor programmed to determine the location of the GPS receiver 20 in the coordinate system of the structure being inspected and then retrieve or generate a calibration file containing calibration data which is dependent on the structural characteristics in the area being interrogated by the flexible ultrasonic transducer array 14. More specifically, the processor inside the calibration database server 26 may be programmed with software that will pull thickness and other material data for the identified location from a CAD file and either: (a) generate a calibration file on the fly based on the 3-D model data; or (b) pull a calibration file from a calibration database. That calibration file is then sent to the transceiver 22, which forwards the calibration information to the data acquisition module 24. The data acquisition module 24 comprises a processor that is programmed to auto-calibrate the flexible ultrasonic transducer array 14 using the calibration data.

Following auto-calibration, the pulser/receiver circuitry of the data acquisition module 24 controls the ultrasonic array to acquire C-scan data. The processor of the data acquisition module 24 is further programmed to convert the C-scan data from the flexible ultrasonic transducer array 14 into a format required by the flexible display panel 16. The C-scan data from the flexible ultrasonic transducer array 14 can also be sent via the transceiver 22 to the C-scan database server 28 for storage.

In accordance with one implementation, the ultrasonic transducer array 14 may comprise two hundred and fifty-six ultrasonic transducer elements 15 (see FIG. 2A) disposed in rows and columns regularly spaced by one quarter of one inch to define a square grid pattern that is four inches wide on each side thereof. However, it should be understood the concepts disclosed herein may applied with equal effect when the ultrasonic transducer array 14 has other numbers of ultrasonic transducer elements, other disposition patterns, and other pattern spacings. In particular, the concepts disclosed herein may be applied when the ultrasonic transducer array 14 has any number of ultrasonic transducer elements arranged in any two-dimensional pattern.

The data acquisition module 24 can operate to energize each ultrasonic transducer element 15 (see FIG. 2A) to send an ultrasonic pulse into an inspected structure and then receive an electrical signal generated by the sensor when an ultrasonic echo signal returns from the structure. Ultrasonic pulses traveling through a structure tend to reflect from surfaces, edges, and other discontinuities such as damage in the structure. A returning ultrasonic echo signal can include multiple time-distributed echo pulses reflected from surfaces and edges that are expected and from damage that deserves investigation and repair. The electrical signal generated by each ultrasonic transducer element 15 conveys amplitude and time data corresponding to the amplitudes and arrival times of echo pulses within the ultrasonic echo signal. The amplitude and time data can be used to discriminate damage-related echo pulses from echo pulses reflected from undamaged features of a structure. After the data acquisition module 24 energizes an ultrasonic transducer element 15 and collects amplitude and time data therefrom, a brief period of quiescence then passes before the controller energizes another ultrasonic transducer element 15. By maintaining pulse-echo operations of each ultrasonic transducer element 15 separate in time from operations of other ultrasonic transducer elements, cross-talk among the ultrasonic transducer elements is avoided and the data collected from each ultrasonic transducer element 15 can be associated with the respective position of each ultrasonic transducer element. Thus, when the ultrasonic transducer array 14 is disposed against a structure, the data collected from the ultrasonic transducer elements 15 can be associated with localized properties of the structure at the respective positions of the ultrasonic transducer elements 15. The data acquisition module converts the acquired ultrasonic data into imaging data suitable for display on the flexible display panel 16. The flexible display panel 16 graphically displays the data for interpretation by a user toward identifying damage in an inspected structure.

Figure 4A:
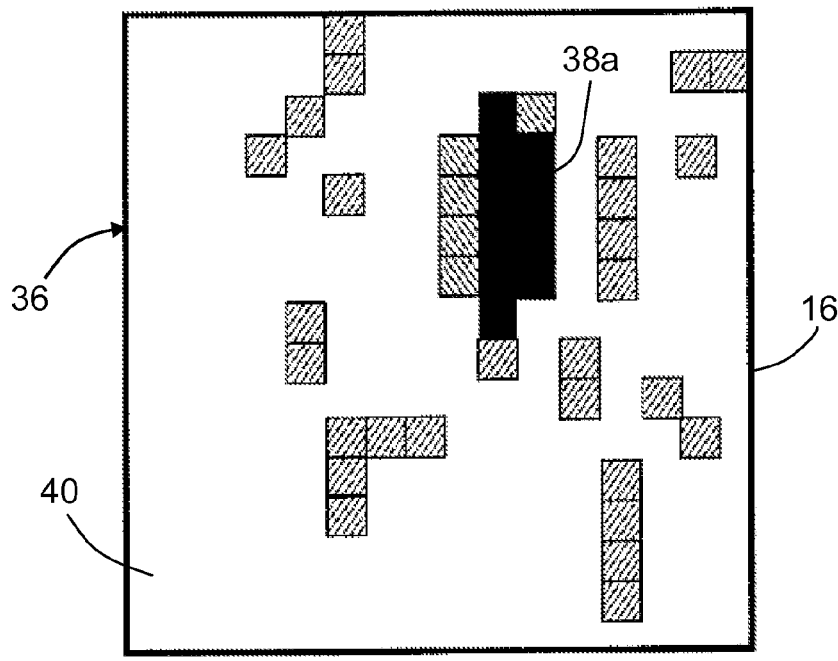
FIG. 4A is a simulated C-scan image of a portion of an inspected aircraft structure, the image showing simulated features including an elongate damage.
Figure 4B:
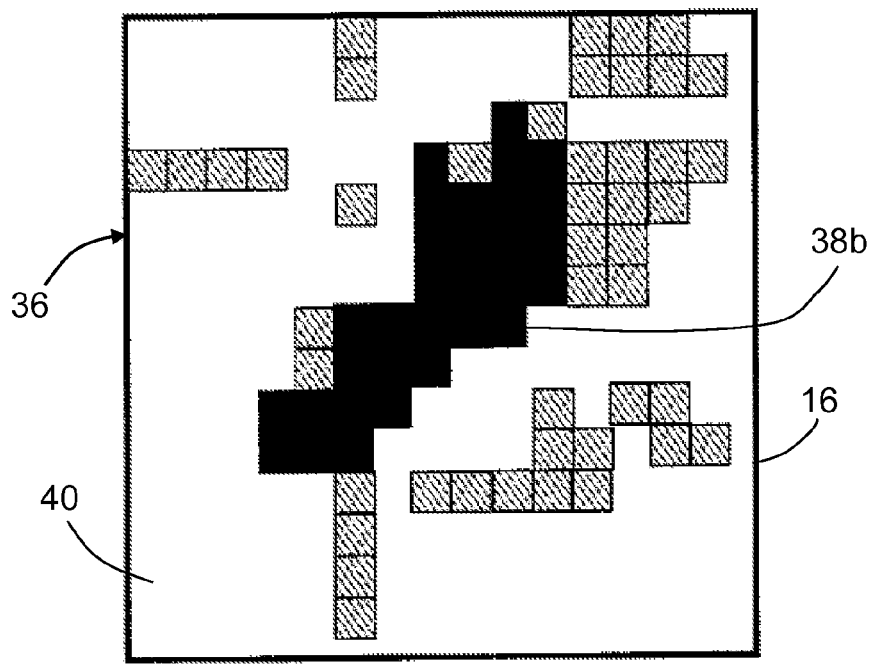
FIG. 4B is another simulated C-scan image of another portion of an inspected aircraft structure, the image showing simulated features including damage distributed across an area.

For example, the flexible display panel 16 may display a simulated echo-amplitude C-scan image of a portion of an inspected structure of the type graphically depicted in FIGS. 4A and 4B. In FIG. 4A, the simulated C-scan image 36 shows simulated features including an elongate damage 38A as distinguished by pixel colorations from an undamaged background area 40 corresponding to an undamaged portion of the structure being inspected. In FIG. 4B, the simulated C-scan image 36 shows simulated features including damage 38B distributed across an area as distinguished by pixel colorations from the undamaged background area 40. The simulated data shown in the displays of FIGS. 4A and 4B represent real data generated using a flexible ultrasonic transducer array 14 having at least two hundred and fifty-six sensors disposed along sixteen rows and sixteen, as is evident in the regularly spaced two-dimensional rectangular matrix of pixels in the flexible display panel 16. Each particular pixel corresponds to a particular ultrasonic transducer element of the ultrasonic transducer array 14, in one-to-one correspondence.

The flexible display panel 16 can display an echo amplitude C-scan image in which the coloration of each pixel corresponds to an amplitude of a portion of an echo signal. In particular, the coloration of each pixel relates to the amplitudes of echo pulses present in a time-gated portion of the waveform detected by a corresponding ultrasonic transducer element. The initiating and closing times of the time gate are established by choice to closely follow and precede front-surface and back-surface return pulses. The initiating and closing times can be established so that the ultrasonic inspection device instrument informs an operator of the likely presence or absence of return pulses from any chosen depth range. Any desired depth range, defined between a first depth and a second depth, can be chosen for inspection by establishing or predetermining both a gate-initiating time corresponding to the first depth and a gate-closing time corresponding to the second depth.

The amplitude within the time-gated portion of the waveform can be derived from a smoothed and integrated function of the waveform according to known mathematical principles. The time-gated portion is selected according to considerations that will be discussed in more detail below.

The pixels in the C-scan images 36 of FIGS. 4A and 4B are each colored according to the summed amplitudes of echo pulses present in time-gated portions of corresponding waveforms. Thus, these images are C-scan echo amplitude images that represent the total ultrasonic echo energy reflected from discontinuities between the front and back surfaces of an inspected structure. Pixels having colors that differ from the undamaged background area 40 generally correspond to damaged locations within the inspected structure. The damage revealed by the pixels in the damaged areas 38A and 38B in FIGS. 4A and 4B respectively reside between the front and back surfaces of the inspected structure. The areas 38A and 38B graphically display images of the damage. The size, disposition, and severity of the damage are revealed by the sizes, dispositions, and colorations of the areas 38A and 38B in the C-scan image 36.

The descriptions herein refer to rows and columns of sensors and pixels distributed along horizontal and vertical axes as a convenient convention in describing two-dimensional arrangements of ultrasonic transducer elements and pixels. It should be understood that the flexible ultrasonic transducer array 14 can be disposed across an area of a structure in almost any arbitrary orientation. Thus, the described axes need not correspond to any vertical axis demonstrated by a plumb line or any horizontal axis such as those along the floor of a hangar where aircraft are inspected.

Furthermore, the C-scan images depicted in FIGS. 4A and 4B generally relate greater echo pulse amplitudes to darker pixel colorations as another convenient convention for the purpose of illustrating subjects of these descriptions. Lighter pixel colorations could just as well be related to greater echo pulse amplitudes in an alternative convention. Indeed, the correlation of the amplitude of an echo pulse to the coloration of a corresponding pixel can be selected according to any desired function or mapping and a color legend may be provided. Though the figures described herein generally provide black and white images, these descriptions relate as well to images comprising pixels having any number of colors such as blue, green, yellow, and red. These descriptions relate to almost any pixel coloring convention, shading convention, or pixel character convention by which an operator may discern information provided by graphically displayed pixels.

The embodiment depicted in FIG. 1 provides several advantages. For example, the flexible ultrasonic transducer array 14 and flexible display panel 16 allow the wireless flexible ultrasonic inspection device 2 to conform to a variety of surface contours such that the inspection system is suitable for field-level inspections of any number of structures. In addition, the wireless flexible ultrasonic inspection device 2 is lightweight, portable, and adaptable to a variety of structures, including aircraft. Because the flexible display panel 16 is positioned directly on the structure and may display an image while positioned thereon, the potential for error in transferring the location of the flaw onto the structure is reduced. The wireless flexible ultrasonic inspection device 2 may also be set up quickly and display images on the flexible display panel 16 in a relatively short period of time after set-up. The wireless flexible ultrasonic inspection device 2 also provides quantitative image-based data that conventional hand-held flaw detector ultrasonic testing cannot provide.

Figure 5:
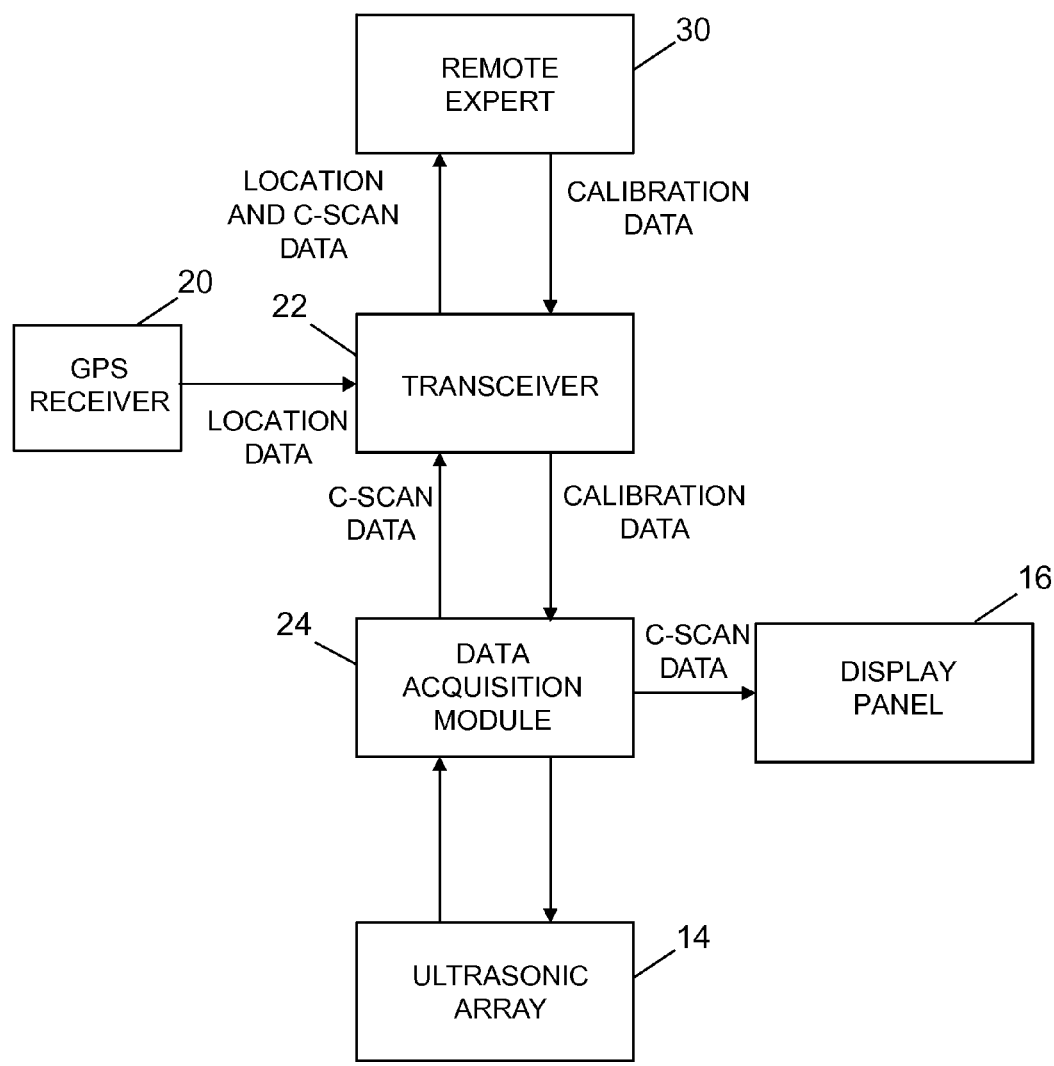
FIG. 5 is a block diagram identifying some components of a wireless flexible ultrasonic inspection device that can communicate wirelessly with a remotely located NDI expert.

In some situations, it may desirable to involve a remotely located (i.e., off-site) NDI expert in the set-up and/or inspection procedures performed at the inspection site. In accordance with an alternative embodiment depicted in FIG. 5, the location data acquired by the GPS receiver 20 can be transmitted by the transceiver 22 of a wireless flexible ultrasonic transducer device to a remote expert 30. The remote expert 30 may also receive additional location data from other GPS receivers attached to other portions of the structure to be inspected. In alternative embodiments, the remote expert 30 can receive a message identifying the location of the flexible ultrasonic inspection device in the coordinate system of the structure being inspected from an on-site technician, or can mandate the location prior to placement of flexible ultrasonic inspection device by the on-site technician.

Regardless of the method or means by which the remote expert 30 acquires location data representing the locations of the structure (e.g., an aircraft) to be inspected and the location of the flexible ultrasonic inspection device, the remote expert 30 may initiate a computer program that determines the location of the wireless flexible ultrasonic inspection device in the coordinate system of the structure using the location data. This enables the remote expert 30 to then generate a calibration file on the fly based on 3-D model data for the inspected structure or pull a calibration file from a calibration database. The calibration data is then sent to the transceiver 22, which forwards the calibration data to the data acquisition module 24 as previously described. The calibrated data acquisition module 24 can then control the flexible ultrasonic transducer array 14 and the flexible display panel 16 as previously described. The remote expert 30 can provide real-time guidance to the on-site technician during the ultrasonic inspection to avoid errors. During the inspection procedure, the transceiver 22 can transmit the C-scan data to the remote expert 30 for review. Optionally, the data acquisition module could be programmed to control the flexible ultrasonic transducer array so that a predetermined number of locations on the flexible ultrasonic transducer array gather A-scan data that can be provided to a remote expert in a saved/transmitted data file.

Figure 6:
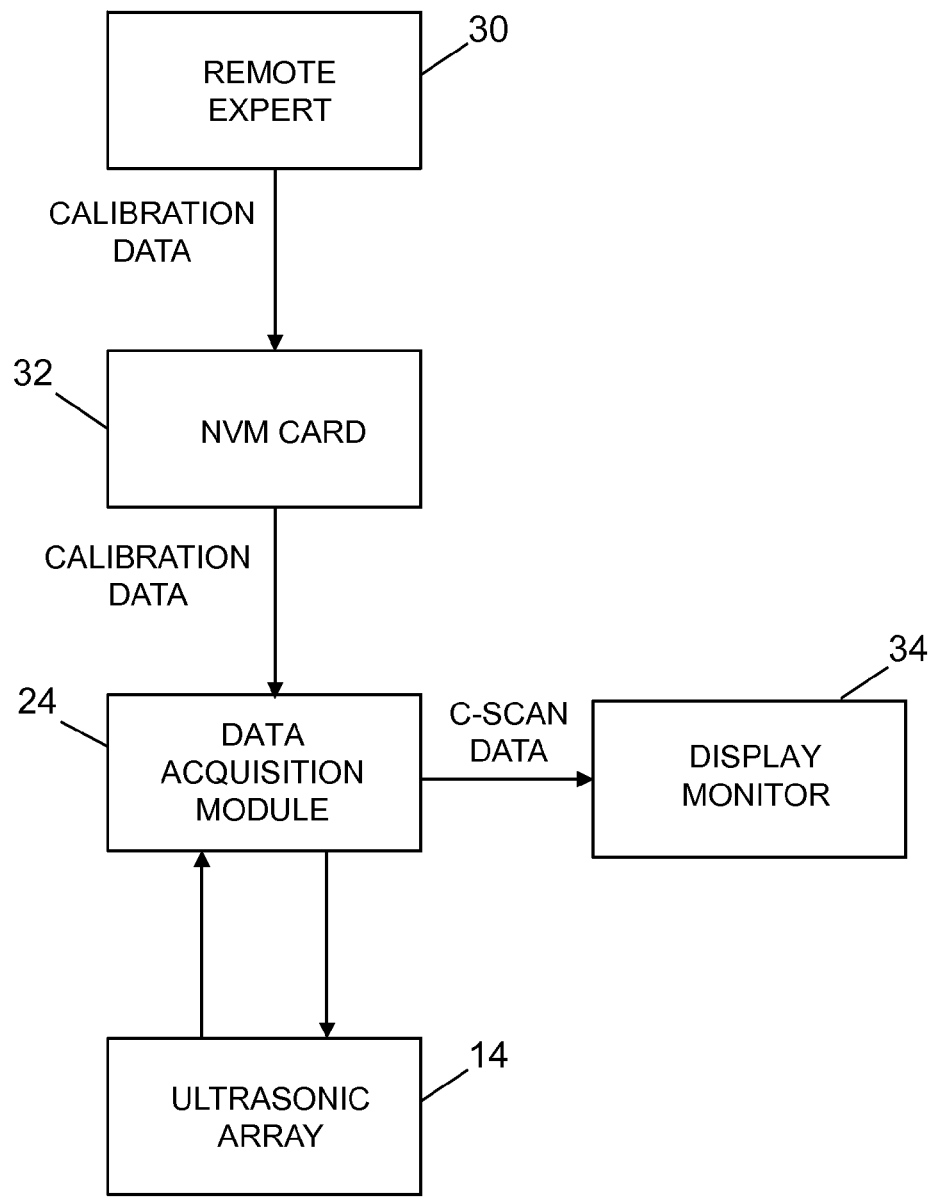
FIG. 6 is a block diagram identifying some components of an ultrasonic inspection system wherein a data acquisition module can be calibrated based on information stored in a pluggable nonvolatile memory card.

In accordance with alternative embodiments, the remote expert 30 can deliver the calibration file to the inspection site in the form of a nonvolatile memory card 32, as shown in FIG. 6. The calibration file is stored on the nonvolatile memory card 32 by the remote expert 30 and then the nonvolatile memory card 32 is plugged into a socket of the data acquisition module 24. The data acquisition module 24 is then auto-calibrated using the calibration data in the calibration file. The ultrasonic data acquired by the calibrated data acquisition module 24 can be displayed on a flexible display panel or a display monitor 34 in a manner consistent with that calibration file. In this case the remote expert 30 may know the location of the flexible ultrasonic transducer array either by communication with the on-site technician or through a procedure callout or airline query. The non volatile memory card 32 could also be full of pre-made calibrations for various areas on the structure.

Figure 7:
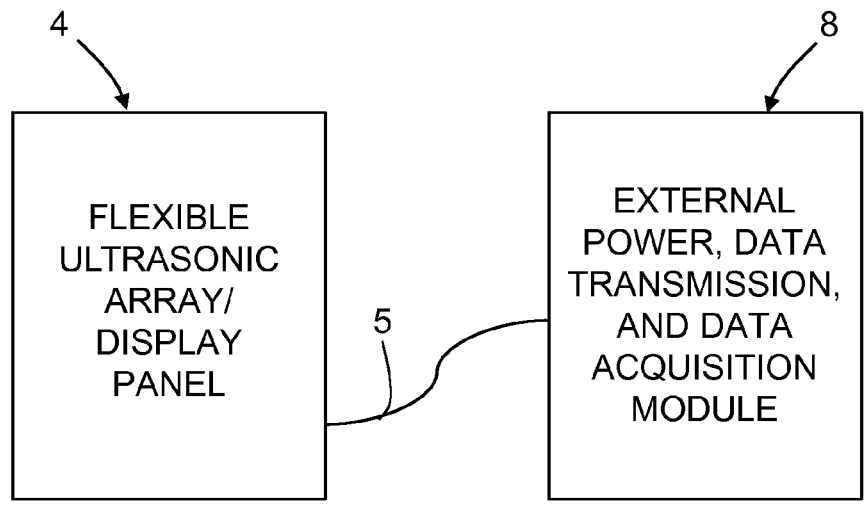
FIG. 7 is a block diagram representing an architecture of one modular ultrasonic inspection system that employs at least some of the concepts proposed herein.

FIG. 7 is a block diagram representing an architecture of a modular ultrasonic inspection system that employs at least some of the concepts proposed herein. The system depicted in FIG. 7 comprises a flexible ultrasonic inspection device 4 that is electrically connected via an electrical cable 5 to a separate external module 8. The electrical cable has plugs (not shown in the drawings) at opposing ends thereof capable of being coupled to and uncoupled from the flexible ultrasonic inspection device 4 and the external module 8. The flexible ultrasonic inspection device 4 comprises a flexible ultrasonic transducer array sandwiched between a flexible delay line substrate and a flexible display panel. The external module 8 comprises a source of electrical power, data transmission means (such as the transceiver previously described), and data acquisition means (such as a processor that performs the same functions as those performed by the previously described data acquisition module, enabling the flexible display panel to display images simulating the structure that was interrogated by the flexible ultrasonic transducer array. The data acquisition means are configured to communicate with the flexible ultrasonic inspection device 4 via the electrical cable 5. A GPS receiver (not shown) may be attached to the flexible ultrasonic inspection device 4 (as previously described). In the alternative, the GPS receiver may be part of the external module 8 if the distance between the flexible ultrasonic inspection device 4 and the external module 8 is either known or minimal and, depending on the resolution of the positioning system, negligible.

Figure 8:
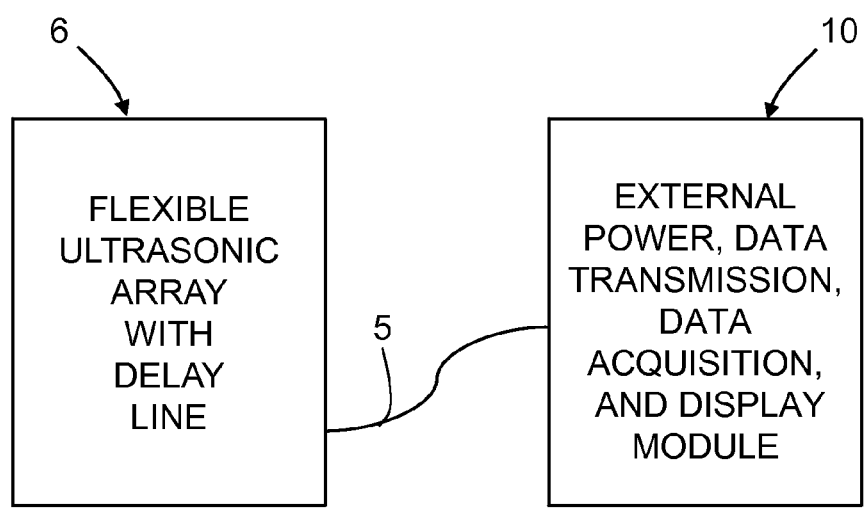
FIG. 8 is a block diagram representing an architecture of another modular ultrasonic inspection system that employs at least some of the concepts proposed herein.

FIG. 8 is a block diagram representing an alternative architecture of a modular ultrasonic inspection system that employs at least some of the concepts proposed herein. The system depicted in FIG. 8 comprises a flexible ultrasonic inspection device 6 that is electrically connected (via an electrical cable 5) to a separate external module 10. The flexible ultrasonic inspection device 6 comprises a flexible ultrasonic transducer array attached to a flexible delay line substrate. The external module 10 comprises a source of electrical power, a display monitor, data transmission means (such as the transceiver previously described), and data acquisition means (such as a processor that performs the same functions as those performed by the previously described data acquisition module, enabling the display monitor to display images simulating the structure that was interrogated by the flexible ultrasonic transducer array. A GPS receiver (not shown) may be attached to the flexible ultrasonic inspection device 6. In the alternative, the GPS receiver may be part of the external module 10.

Figure 9:
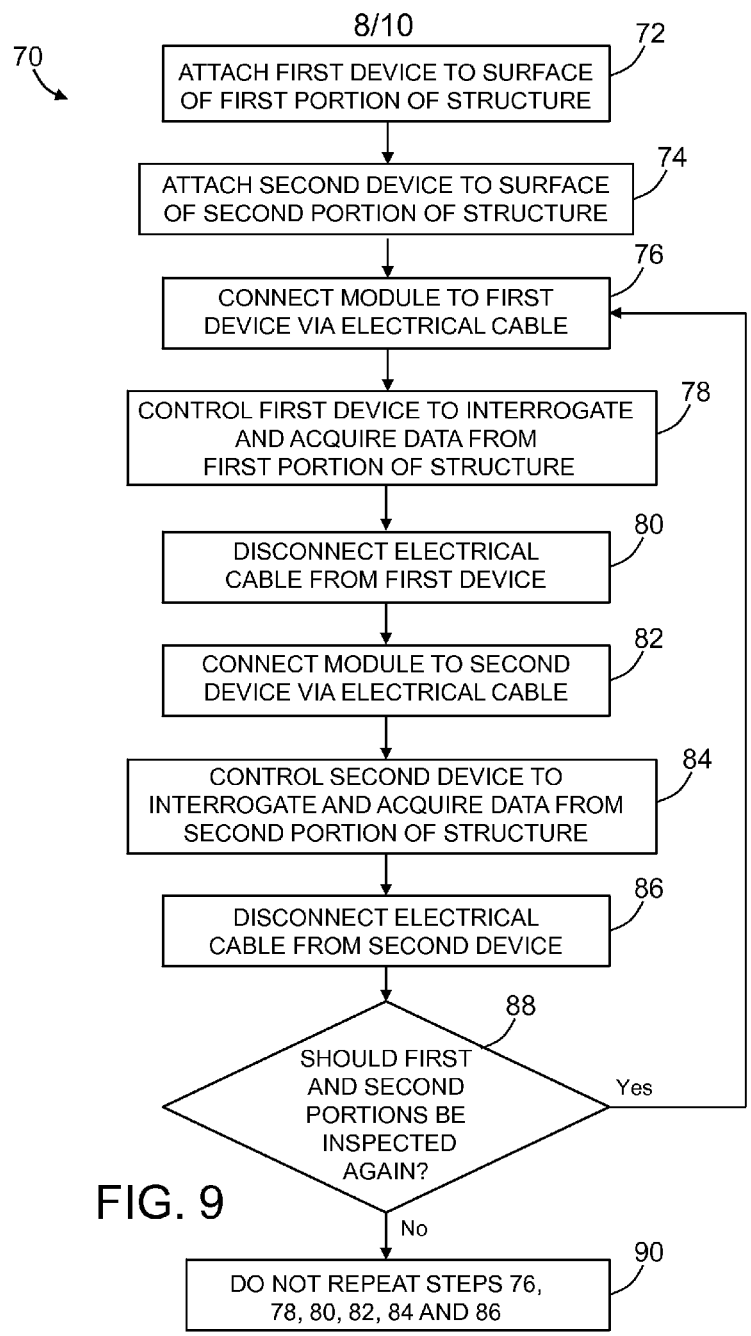
FIG. 9 is a flowchart identifying steps of a method for ultrasonic inspection of multiple sites on a structure wherein respective flexible ultrasonic inspection devices are attached to the surface at each site and left in place to allow periodic inspection using an external module that can be connected to each flexible ultrasonic inspection devices in turn.

In accordance with either of the architectures depicted in FIGS. 7 and 8, the external module can be connected in turn to respective flexible ultrasonic inspection devices attached at multiple sites on the structure to be inspected. FIG. 9 is a flowchart identifying steps of a method 70 for ultrasonic inspection of multiple sites on a structure wherein respective flexible ultrasonic inspection devices are attached to the surface at each site and left in place to allow periodic inspection using an external module that can be connected to each flexible ultrasonic inspection devices in turn.

In accordance with the embodiment depicted in FIG. 9, the method 70 comprises the following steps: attaching a first flexible ultrasonic inspection device to a surface of a first portion of the structure (step 72), wherein the first flexible ultrasonic inspection device comprises a first flexible substrate and a first two-dimensional flexible ultrasonic transducer array attached to the first flexible substrate; attaching a second flexible ultrasonic inspection device to a surface of a second portion of the structure (step 74), wherein the second flexible ultrasonic inspection device comprises a second flexible substrate and a second two-dimensional flexible ultrasonic transducer array attached to the second flexible substrate; connecting a module to the first flexible ultrasonic inspection device via an electrical cable (step 76), which module comprises pulser/receiver circuitry which is configured to control interrogation and data acquisition by the first flexible ultrasonic transducer array during inspection of the first portion of the structure and is further configured to control interrogation and data acquisition by the second flexible ultrasonic transducer array during inspection of the second portion of the structure; controlling the first flexible ultrasonic transducer array to interrogate and acquire data from the first portion of the structure while the module is connected to the first flexible ultrasonic inspection device (step 78); disconnecting the electrical cable from the first flexible ultrasonic inspection device after completion of step 78 (step 80); connecting the module to the second flexible ultrasonic inspection device via the electrical cable (step 82); controlling the second flexible ultrasonic transducer array to interrogate and acquire data from the second portion of the structure while the module is connected to the second flexible ultrasonic inspection device (step 84); disconnecting the electrical cable from the second flexible ultrasonic inspection device after completion of step 84 (step 86); and determining whether the first and second portions of the structure should be inspected again (e.g., at a later date) or not (step 88). If the result of step 88 is a determination that the first and second portions of the structure should be inspected again, then the method returns to step 76 and the process is repeated. If the result of step 88 is a determination that the first and second portions of the structure should not be inspected again, then the method does not return to step 76 or repeat the process (step 90). At that time, the attached flexible ultrasonic inspection devices could be removed from the structure.

The method shown in FIG. 9 may be used in situations where a multiplicity of potential damage sites in a structure are scheduled to inspected periodically. This method is especially useful when the damage sites are located in difficult-to-access spaces. A single external module having a display monitor could be placed at an accessible location and then connected to each ultrasonic inspection device in turn via an electrical cable. The on-site technician can view C-scan images in turn and take appropriate action based on what those images indicate about the structural integrity at the potential damage sites.

Figure 10:
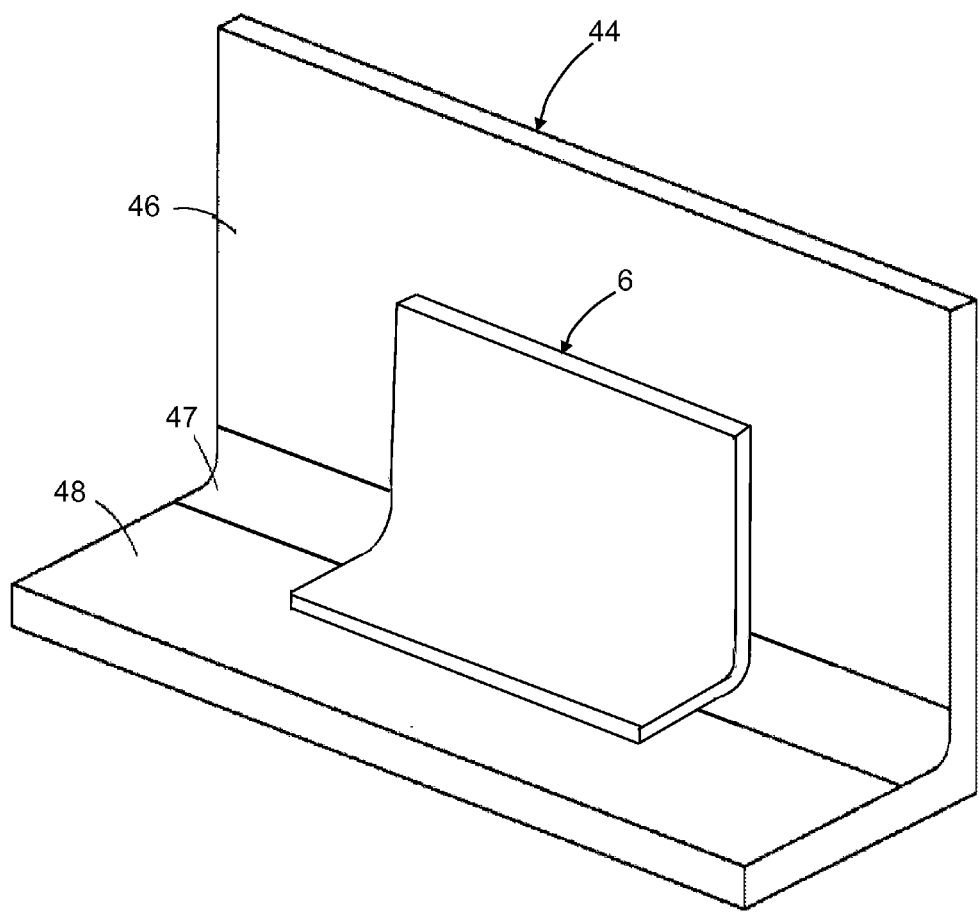
FIG. 10 is a diagram representing an isometric view of a flexible ultrasonic inspection device lying against and acoustically coupled to a portion of an integrally stiffened wing box with a radiused surface.

In accordance with other embodiments, a flexible ultrasonic inspection device may be designed to handle radiused surfaces. One embodiment would be "L-shaped" with a short radius that is flexible enough to fit in radiused surfaces having a range of radii. The system configuration would be similar to that shown in FIG. 8 in order to minimize the number of flexible layers (e.g., by not including a flexible display panel) to allow for more flexibility. In the scenario shown in FIG. 10, a flexible ultrasonic inspection device 6 (consisting of a flexible delay line substrate is lying against and acoustically coupled to a portion 44 of a generalized integrally stiffened wing box (made of composite material) with a radiused surface. The depicted portion 44 of the integrally stiffened wing box comprises a skin 48 connected to a spar web 46 by means of a radiused surface 47, which is a filleted join region which connects the spar web 46 to the skin 48. Like in embodiment depicted in FIGS. 1 and 2, a power source, a GPS receiver, data transmission means, and data acquisition means may be mounted to the flexible delay line substrate in areas meant to cover flat sections of the part being inspected. For radiused surfaces that have larger radii, it may be possible to keep a flexible display panel mounted on the flexible ultrasonic transducer array instead of using an external module. Another embodiment would consist of a flat area array, but with one marginal region made of flexible material to allow that marginal region to fit the curvature of the radiused surface being inspected. Arrays having curved marginal regions of different radii could be manufactured depending on the curvature of the radiused surface one needs to fit to.

The ultrasonic inspection systems disclosed above can be used to measure thickness, depth or distance by timing echoes. In order to convert these time measurements into distance measurements, the ultrasonic inspection system can be calibrated with the speed of sound in the inspected structure as well as any necessary zero offset. This process is commonly referred to as velocity/zero calibration. The accuracy of any ultrasonic thickness, depth or distance measurement is dependent on the accuracy of the calibration. Calibrations for different materials and transducers can be stored and retrieved, as previously described.

The automated calibration method can entail, for example, establishing the speed of propagation of ultrasonic pulses in the inspected material in order to correlate time of flight (TOF) measurements with material depths, and selecting time and depth axes ranges and time-gate settings for the display of C-scan images. Depth is derived from the TOF measured between the dispatch of an ultrasonic pulse into a structure and the return of an echo pulse. If the speed of propagation of ultrasonic pulses is known for a particular inspected material, the vertical axis of the scan window can be calibrated toward particular linear depth dimensions according to the TOF of each echo pulse.

The methodology disclosed herein automates the calibration of ultrasonic inspection systems through the use of three-dimensional (3-D) CAD data representing a 3-D model of the structure to be inspected. By basing calibration on a CAD model, it is possible to pull more data into location-specific inspections. CAD model data (i.e., also referred to herein as "structural data") may comprise information concerning one or more of the following structural features of the test object at or in the area containing the target position: physical dimensions, material characteristics, fastener locations, structural anomalies, an alteration or a repair to the test object, average paint thickness, hidden stringers, electromagnetic effects (EME) protection layers and other features that may not be accounted for in a general inspection.

The CAD model database also includes information concerning the structure being inspected, which information can be used to automatically calibrate the ultrasonic inspection system that will be used to inspect that area. The CAD model contains data about the airplane structure in the area of the inspection site, including information concerning one or more of the following: (a) material type (average attenuation, which will be determined through involved testing of many composite standards); (b) material thickness; (c) underlying structure (can be displayed on inspection instrument to help qualify odd signals); (d) presence of sealant (gain can be adjusted to account for reduced backwall signal); (e) presence of an EME layer; (f) average paint thickness; (g) fastener location (the user can be warned about odd signals if they are positioned directly over a fastener); and (h) the presence of repairs in the inspection area (if the CAD file has been kept up to date by the airline or other user). Such CAD model data can be used to generate a calibration file for the structure and provide the inspector with the situational awareness needed to make informed decisions about the inspection.

Figure 11:
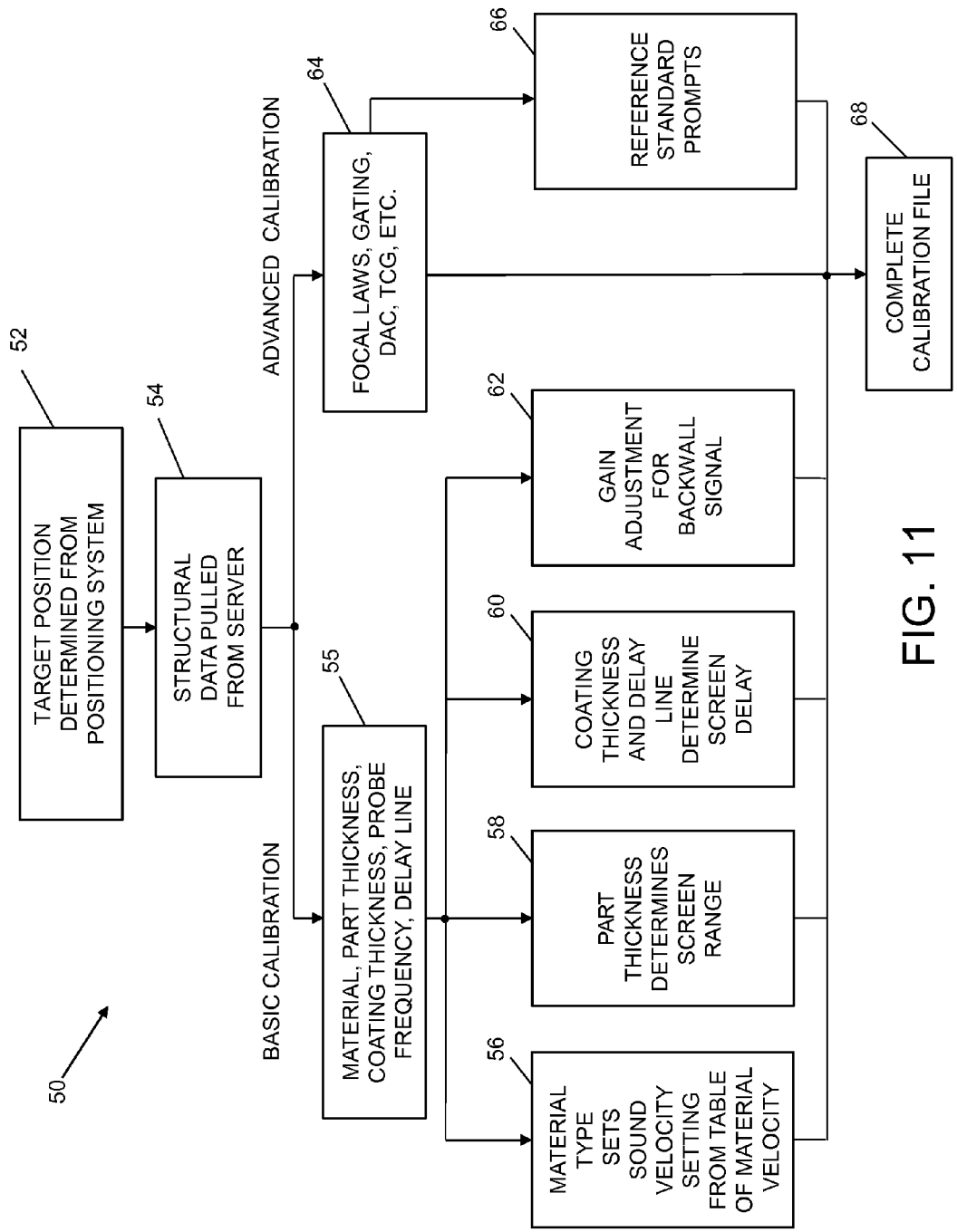
FIG. 11 is a flowchart identifying steps of a method for generating a calibration file based on a target position on a surface of a test object (determined using a positioning system) and associated structural data retrieved from a server.

FIG. 11 is a flowchart identifying steps of a method 50 for generating a calibration file using a positioning system. First, the target position (i.e., the place on the surface of the test object where the underlying structure is to be inspected) is determined using the positioning system (step 52). Then the structural data associated with that target position is pulled from a CAD model database server (step 54). A simplified embodiment would involve pre-made procedures being attributed to certain areas on the airplane that are then loaded based on initial target position at the start of the inspection.

Still referring to FIG. 11, it can be seen that the structural data can be used to perform a basic calibration or an advanced calibration (which may include the basic calibration and additional calibration). In the basic calibration, calibration parameters such as material, part thickness, coating thickness, probe frequency, and flexible delay line are selected based on the relevant structural data (step 55). The material type sets the sound velocity setting from a table of material velocities (step 56). The part thickness determines the screen range (step 58). The coating thickness and flexible delay line determine the screen delay (step 60). In addition, the gain can be adjusted to take into account the backwall signal (step 62).

In accordance with an advanced calibration methodology, additional calibration parameters, such as focal laws, gating, Distance-Amplitude Correction (DAC), and Time-Compensated Gain (TCG), can be determined by a computer which is programmed with calibration software for processing the structural data (step 64). Optionally, reference standard prompts can be automatically generated for more advanced calibrations operations (step 66). The inspector could be automatically prompted to a reference standard and given instructions at such times.

Finally, all of the calibration parameters are organized in accordance with a specified format to complete the calibration file (step 68). That calibration file is then used to calibrate the ultrasonic inspection system.

The use of CAD model data enables automation of a process that generally requires a trained Nondestructive Testing (NDT) inspector. As a result, it removes a degree of human error from the calibration process. This cuts training costs and reduces inspection times by not requiring a trained NDT inspector to perform each and every inspection.

While apparatus and methods have been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising at least one processing unit (e.g., a central processing unit, an integrated circuit or an arithmetic logic unit).

The method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. An ultrasonic inspection device comprising:
a flexible assembly comprising a flexible ultrasonic transducer array having first and second faces, and a flexible delay line substrate acoustically coupled to said first face of said flexible ultrasonic transducer array;
data acquisition module configured to control pulsing of and data acquisition by said flexible ultrasonic transducer array;
a global positioning system receiver configured to determine a location of said global positioning system receiver;
a transceiver configured to communicate with said data acquisition module and said global positioning system receiver; and
a battery electrically coupled to said data acquisition module, said global positioning system receiver, and said transceiver for providing power thereto,
wherein said data acquisition module, said global positioning system receiver, said transceiver, and said battery are physically attached to said flexible assembly.

2. The ultrasonic inspection device as recited in claim 1, further comprising adhesive adhered to portions of a surface of said flexible delay line substrate that faces away from said flexible ultrasonic transducer array.

3. The ultrasonic inspection device as recited in claim 1, wherein said flexible assembly further comprises a flexible display panel overlapping at least a portion of said second face of said flexible ultrasonic transducer array, and said data acquisition module is further configured to receive ultrasonic data from said flexible ultrasonic transducer array in a first format, convert said ultrasonic data in said first format to ultrasonic data in a second format suitable for display, and send said ultrasonic data in said second format to said flexible display panel.

4. The ultrasonic inspection device as recited in claim 3, wherein said data acquisition module comprises:
pulser-receiver circuitry electrically coupled to receive said ultrasonic data in said first format from said flexible ultrasonic transducer array; and
a processor programmed to convert said ultrasonic data in said first format to ultrasonic data in said second format and control said flexible display panel to display said ultrasonic data in said second format.

5. The ultrasonic inspection device as recited in claim 3, wherein said flexible display panel comprises a polymeric substrate, a multiplicity of pixels arranged in rows and columns in or on said polymeric substrate, and a multiplicity of thin-film transistors disposed in or on said polymeric substrate and electrically coupled to respective pixels of said multiplicity of pixels.

6. The ultrasonic inspection device as recited in claim 5, wherein said pixels comprise respective organic light-emitting diodes.

7. The ultrasonic inspection device as recited in claim 5, wherein said pixels comprise liquid crystal.

8. The ultrasonic inspection device as recited in claim 1, wherein said data acquisition module, said global positioning system receiver, said transceiver, and said battery are physically attached to a portion of said flexible delay line substrate that extends beyond a perimeter of said flexible ultrasonic transducer array.

9. The ultrasonic inspection device as recited in claim 1, wherein said flexible ultrasonic transducer array comprises a multiplicity of ultrasonic transducer elements arranged in rows and columns.

10. The ultrasonic inspection device as recited in claim 1, wherein said flexible ultrasonic transducer array comprises a plurality of mutually parallel transmit electrodes and a plurality of mutually parallel receive electrodes which overlap with, but are not parallel to, said transmit electrodes.

11. The ultrasonic inspection device as recited in claim 1, further comprising a computer system programmed to receive said location data from said transceiver, and then generate or retrieve a calibration file containing calibration data which is a function of material properties of a structural component to be inspected.

* * * * *